United States Patent [19]

Wang

[11] Patent Number: 4,634,787

[45] Date of Patent: Jan. 6, 1987

[54] PROCESS FOR PREPARING (2,2,2-TRIHALO-1, 1-DIHYDROCARBYL-ETHOXY) TRIHYDROCARBYLSILANES

[75] Inventor: Pen-Chung Wang, Midland, Mich.

[73] Assignee: The Dow Chemical Company, Midland, Mich.

[21] Appl. No.: 796,121

[22] Filed: Nov. 8, 1985

[51] Int. Cl.$^4$ .............................. C07F 7/08; C07F 7/18
[52] U.S. Cl. ....................................... 556/470
[58] Field of Search ........................................ 556/470

[56] References Cited

U.S. PATENT DOCUMENTS

| | | | |
|---|---|---|---|
| 3,856,843 | 12/1974 | Nagai et al. ..................... | 556/470 X |
| 4,375,548 | 3/1983 | Wang et al. ........................ | 556/470 |
| 4,377,706 | 3/1983 | Hallgren ........................ | 556/470 X |
| 4,383,120 | 5/1983 | Yate ................................... | 556/470 |

OTHER PUBLICATIONS

Fujita et al., "J.A.C.S.", vol. 107, No. 13, pp. 4085–4087, 6/26/85.
*Synthesis*, 131 (1971).
*Synthesis*, 626 (1980).

*Primary Examiner*—Paul F. Shaver

[57] ABSTRACT

A process for forming trihalomethylsiloxanes by contacting a trihalosilane with a carbonyl in the presence of the fluoride ion. These compounds are used to form α-substituted acid chlorides.

22 Claims, No Drawings

PROCESS FOR PREPARING (2,2,2-TRIHALO-1,1-DIHYDROCARBYL-ETHOXY) TRIHYDROCARBYLSILANES

BACKGROUND OF THE INVENTION

This invention relates to a process for preparing (2,2,2-trihalo-1,1-dihydrocarbylethoxy)trihydrocarbylsilanes (hereinafter referred to as Wang compounds).

By subjecting Wang compounds to mildly acidic conditions, they may be converted to their corresponding trihalomethyl-substituted hydroxyl-containing compounds which are useful intermediates for the preparation of α-substituted acid chlorides.

W. Reeve, in *Synthesis*, 131 (1971) discloses applications adapted to the use of trichloromethyl carbinol compounds. In particular, the reference describes a wide variety of reactions between trichloromethyl carbinols and reactive nucleophiles such as to prepare α-substituted acid chlorides, amino acids and mercapto acids.

Previous techniques for the preparation of Wang compounds include U.S. Pat. No. 4,375,548. The process of U.S. Pat. No. 4,375,548 disadvantageously requires elevated reaction temperatures.

Previously known techniques for the preparation of aryl-(trichloromethyl)carbinols also include the reaction of aromatic hydrocarbons with trichloroacetaldehyde in the presence of a Lewis acid or the reaction of arylmagnesium bromide with trichloroacetaldehyde.

It is also known to prepare aryl-(trichloromethyl)carbinols and alkyl-(trichloromethyl)carbinols by the reaction of carbonyl compounds with chloroform in the presence of caustic and a phase-transfer catalyst such as a quaternary ammonium salt.

Additional processes include electrochemical reduction of carbon tetrachloride and subsequent reaction of the carbon trichloride anions with electrophilic aldehydes. In the presence of hydrogen-containing solvents, e.g., chloroform, the intermediate reaction product abstracts a proton from the solvent, thereby preparing the desired trichloromethyl-substituted carbinol compound.

These processes all disadvantageously form stoichiometric by-products. It would be desirable to have a process to form Wang compounds without forming a stoichiometric amount of one or more by-products.

SUMMARY OF THE INVENTION

The present invention is a process for forming Wang compounds without forming stoichiometric amounts of by-products. The process comprises contacting (1) a silane of the formula, $$X_3CSi(R^1)_3, \quad (I)$$

in which each X is independently halo and each $R^1$ is independently a monovalent hydrocarbon radical, or one $R^1$ is a monovalent hydrocarbon radical, and the remaining two $R^1$ are collectively a divalent hydrocarbon radical, or all three $R^1$ are collectively a trivalent hydrocarbon radical, with (2) a carbonyl of the formula,

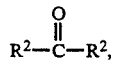

(II)

in which each $R^2$ is independently hydrogen or a monovalent hydrocarbon radical, provided at the most one $R^2$ is hydrocarbon, or both $R^2$ are collectively a divalent hydrocarbon radical, in the presence of a catalytic amount of the fluoride ion under conditions sufficient to produce a Wang compound of the formula,

in which X, $R^1$ and $R^2$ are as previously defined. The hydrocarbon moieties represented by $R^1$ and $R^2$ may contain one or more essentially unreactive substituents and may contain one or more heteroatoms. This process advantageously does not form stoichiometric by-products, thus enabling the product to be obtained without separation and results in a high yield of the desired product. This invention is a process for preparing reactive carbinol precursors having protected hydroxyl functionality. These precursors are useful to prepare α-substituted acid chlorides, amino acids and mercapto acids.

DETAILED DESCRIPTION OF THE INVENTION

The silanes suitably employed in the practice of this invention are represented by formula (I). Preferably, in formula (I), each $R^1$ is independently a monovalent hydrocarbon containing from 1 up to about 50 carbon atoms and which may contain one or more substituents and which may contain one or more heteroatoms. More preferred $R^1$ contain from 1 to about 20 carbon atoms. Most preferred $R^1$ are methyl. In formula (I), preferably, each X is independently chloro or bromo. More preferably, each X is the same and is chloro or bromo. Even more preferably, each X is chloro. Preferred silanes are trichloromethylsilanes and the most preferred silane is trichloromethyltrimethylsilane.

For the purposes of this invention, the term heteroatom means an atom other than hydrogen or carbon.

For the purposes of this invention, all substituents, heteroatoms and diluents do not react themselves under the reaction conditions or react to a degree insufficient to prevent the formation of Wang compounds.

Methods for preparing these silanes are well-known in the art (see, for example, Hergott et al., "Eine Einfache Synthese von Trichloromethyltrimethylsilan und Carbon Säure-trimethylsilylestern," *Synthesis*, 626 (1980), now incorporated by reference).

Preferred are carbonyls in which each $R^2$ is independently hydrogen, a monovalent hydrocarbon moiety, provided at the most, one $R^2$ is hydrogen or both $R^2$ are collectively a hydrocarbylene radical, $R^2$ may contain one or more substituents and may contain one or more heteroatoms. More preferred carbonyls are benzaldehyde, 4-methoxybenzaldehyde, cyclopentanone, cyclohexanone, pentan-3-one and quinone. The most preferred carbonyl compound is benzaldehyde.

The amounts of carbonyl and silane compounds most advantageously employed in the practice of this invention are dependent on a variety of factors including the particular carbonyl and silane compounds employed; the reaction temperature; the diluent, if any; and its concentration. In general, the amounts of reactants employed are not particularly critical to the practice of the present invention, except that the silane reaction should be in slight molar excess. Preferably the molar ratio of carbonyl compound to silane is less than about 1:1 and more preferably less than about 0.99:1. Preferably the molar ratio of carbonyl compound to silane is greater than about 0.8:1, more preferably greater than about 0.9:1.

The fluoride ion is provided in an effective manner and amount. Preferred is the use of salts such as KF, NaF, CaF₂ and Bu₄NF. Most preferred is the use of Bu₄NF. Preferably, the fluoride ion is present in a concentration more than about 0.05 mole percent based on the combined reactants, more preferably more than about 0.1 mole percent based on the combined reactants and most preferably more than about 0.5 mole percent based on the combined reactants.

Insoluble flouride salts may be assisted by the use of phase-transfer catalysts such as crown ethers and the like, as described in C. M. Starks and C. Liott, *Phase Transfer Catalysts,* Academic Press, 1978.

Preferably, the phase-transfer catalysts are present in an amount less than about 5 mole percent based on the silane reactant and more preferably less than about 2 mole percent.

The reaction may be conducted neat. However, the contact may be in the presence of one or more diluents. The diluents can be one or more liquids. Preferred are organic liquids such as tetrahydrofuran, acetonitrile, nitromethane, toluene, xylenes, chlorobenzene, benzonitrile, glyme, diglyme, methyl tert-butyl ether and hexane. Tetrahydrofuran is preferred. Molar ratios of diluent to combined reactants in the range of about 1:1 to about 500:1 can be employed. Preferably, the molar ratio of diluent to combined reactants is greater than about 5:1, more preferably greater than about 10:1 and most preferably greater than about 20:1. Preferably, the molar ratio of diluent to combined reactants is smaller than about 200:1, more preferably smaller than about 100:1 and most preferably smaller than about 25:1. The contact may occur in reactors constructed of glass, steel, glass-lined steel and the like. The reaction mixture is preferably agitated. The reaction conditions most advantageously employed will vary depending on factors such as the specific reactants, their concentrations, the catalyst employed and any diluent. In general, the reaction will proceed at room temperature but the reaction rate will increase as the reaction temperature increases. Reaction temperatures up to and including the reaction mixture's reflux temperature can be advantageously employed. Preferably, the reaction temperature is above about 0° C., more preferably above about 20° C. Preferably, the reaction mixture is refluxed until the desired conversion has taken place.

Preferably, yields of greater than about 70 mole percent, based on the silane reactant; more preferably greater than about 80 mole percent and most preferably more than about 90 mole percent are obtained.

The reaction will proceed in the presence of air but is preferably conducted in an unreactive environment such as that provided by nitrogen blanketing. While the process may be carried out at subatmospheric or superatmospheric pressures, it is typically carried out at atmospheric pressure.

The reaction product is a Wang compound. Preferable Wang compounds are trimethyl(2,2-trichloro-1-phenylethoxy)silane, trimethyl(2,2,2-trichloro-1-(4-methoxyphenyl)ethoxy)silane, trimethyl[(1-(trichloromethyl)cyclopentyl)oxy]silane, trimethyl[(1-(trichloromethyl)cyclohexyl)oxy]silane, (1-ethyl-1-(trichloromethyl)propoxy)trimethylsilane and 4-(trichloromethyl)-4-[(trimethylsilyl)oxy]2,5-cyclohexadien-1-one.

The invention is further illustrated by the following nonlimiting examples.

EXAMPLE 1

Into a 25-ml round-bottom flask equipped with agitation, heating, cooling, reflux, temperature control and gas blanketing means, are added 1.06 g (0.01 mole) of benzaldehyde, 1.90 g (0.01 mole) of trichloromethyltrimethyl silane, Cl₃CSi(CH₃)₃, and 0.05 g (0.0002 mole, 2 mole percent) of Bu₄NF. The reaction mixture is stirred at room temperature for 30 minutes under a nitrogen atmosphere to produce 2.84 g (0.00955 mole) of (2,2,2-trichloro-1-phenylethoxy)silane,

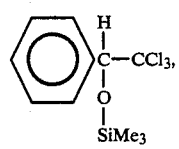

as identified by nuclear magnetic resonance spectroscopic analysis. This is a yield of 96 mole percent based on the silane reactant.

EXAMPLE 2

Example 1 is repeated except that 1.37 g (0.01 mole) of 4-methoxybenzaldehyde,

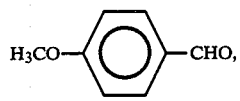

is substituted for benzaldehyde, as the carbonyl compound, thereby producing 2.99 g (0.0096 mole) of trimethyl(2,2,2-trichloro-1-(4-methoxyphenyl)ethoxy)silane,

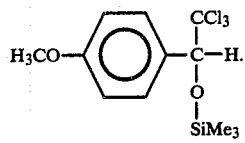

This is a yield of 96 mole percent based on the silane reactant.

EXAMPLE 3

Into a 25-ml round-bottom flask are placed a magnetic stirring rod, 0.84 g (0.01 mole) of cyclopentanone,

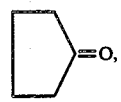

1.90 g (0.01 mole) of trichloromethyltrimethylsilane, Cl₃CSi(CH₃)₃, 0.05 g (0.0002 mole, 2 mole percent based on trichloromethyltrimethylsilane) of Bu₄NF and 10 ml of anhydrous tetrahydrofuran,

as an internal gas chromatograph standard. The flask is warmed with stirring to 90° C. and is allowed to react until a gas chromatograph shows the reactants have been consumed, usually about 2 hours. The product is 2.6 g (0.00958 mole) of trimethyl[(1-(trichloromethyl)-cyclopentyl)oxy]silane,

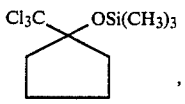

as identified by infrared spectroscopic examination. This is a yield of 96 mole percent based on the silane reactant. The product can be separated from tetrahydrofuran by distillation.

EXAMPLE 4

Example 3 is repeated, except 0.98 g (0.01 mole) of cyclohexanone,

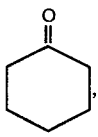

is substituted for cyclopentanone as the carbonyl compound thereby producing 2.73 g (0.00960 mole) of trimethyl[(1-(trichloromethyl)cyclohexyl)oxy]silane,

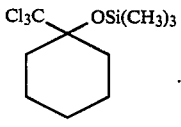

This is a yield of 96 mole percent based on the silane reactant.

EXAMPLE 5

Example 3 is repeated, except 0.86 g (0.01 mole) of pentan-3-one,

is substituted for cyclopentanone as the carbonyl compound thereby producing 2.15 g (0.00775 mole) of (1-ethyl-1-(trichloromethyl)propoxy)trimethylsilane,

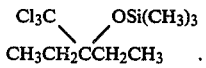

This is a yield of 78 mole percent based on the silane reactant.

EXAMPLE 6

Example 3 is repeated except 1.09 g (0.01 mole) of quinone,

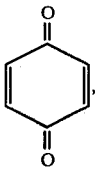

is substituted for cyclopentanone as the carbonyl compound thereby producing 2.70 g (0.00902 mole) of 4-(trichloromethyl)-4-[(trimethylsilyl)oxy]-2,5-cyclohexadien-1-one,

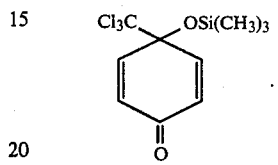

This is a yield of 90 mole percent based on the silane reactant.

The above examples illustrate the high yields of the invented process in various embodiments.

I claim:

1. A process of forming (2,2,2-trihalo-1,1-dihydrocarbylethoxy)trihydrocarbylsilanes (Wang compounds) without forming stoichiometric amounts of by-products comprising contacting (1) a silane of the formula $$X_3CSi(R^1)_3 \qquad (I)$$

in which X is independently halo and each $R^1$ is independently a monovalent hydrocarbon radical, or one $R^1$ is a monovalent hydrocarbon radical, and the remaining two $R^1$ are collectively a divalent hydrocarbon radical, or all three $R^1$ are collectively a trivalent hydrocarbon radical, with (2) a carbonyl of the formula

in which each $R^2$ is independently hydrogen or a monovalent hydrocarbon radical, provided at the most, one $R^2$ is hydrogen, or both $R^2$ are collectively a hydrocarbylene radical, in the presence of a catalytic amount of the fluoride ion under conditions sufficient to produce a Wang compound of the formula,

in which X, $R^1$ and $R^2$ are as previously defined, said hydrocarbon radicals represented by $R^1$ and $R^2$ may contain one or more substituents and may contain one or more heteroatoms.

2. The process of claim 1 in which each $R^1$ is methyl.
3. The process of claim 1 in which X is independently chloro or bromo.
4. The process of claim 3 in which each X is the same and is chloro or bromo.
5. The process of claim 4 in which X is chloro.
6. The process of claim 1 in which one $R^2$ is hydrogen.

7. The process of claim 6 in which the carbonyl is selected from the group consisting of benzaldehyde and 4-methoxybenzaldehyde.

8. The process of claim 7 in which the carbonyl is benzaldehyde.

9. The process of claim 1 in which the contact is in the presence of one or more diluents.

10. The process of claim 9 in which the diluents are tetrahydrofuran, acetonitrile, nitromethane, toluene, benzene, the xylenes, chlorobenylene, benzonitrile, glyme, diglyme, methyl tert-butyl ether or hexane.

11. The process of claim 10 in which the diluent is tetrahydrofuran.

12. The process of claim 1 in which the reaction mixture is heated.

13. The process of claim 12 in which the temperature of the reaction mixture is between about 0° C. and the reflux temperature of the reaction mixture.

14. The process of claim 13 in which the temperature of the reaction mixture is between about 20° C. and the reflux temperature of the reaction mixture.

15. The process of claim 1 in which the reaction proceeds under a nitrogen blanket.

16. The process of claim 1 in which the fluoride ion is provided by the use of a salt selected from the group consisting of KF, NaF, $CaF_2$ and $Bu_4NF$.

17. The process of claim 16 in which the salt is $Bu_4NF$.

18. The process of claim 1 in which the yield is greater than about 70 mole percent based on the combined reactants.

19. The process of claim 15 in which the silane is trichloromethyl trimethyl silane and the fluoride ion is provided by $Bu_4NF$.

20. The process of claim 19 in which the temperature of the reaction mixture is between about 0° C. and the reflux temperature of the reaction mixture.

21. The process of claim 1 in which each $R^2$ is a monovalent hydrocarbon radical.

22. The process of claim 21 in which the carbonyl is selected from the group consisting of cyclopentanone, cyclohexanone, pentan-3-one and quinone.

* * * * *